(12) United States Patent
Lanfermann et al.

(10) Patent No.: US 8,301,237 B2
(45) Date of Patent: Oct. 30, 2012

(54) BIOFEEDBACK SYSTEM AND DISPLAY DEVICE

(75) Inventors: Gerd Lanfermann, Aachen (DE); Richard Daniel Willmann, Siegburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 424 days.

(21) Appl. No.: 12/302,306

(22) PCT Filed: May 14, 2007

(86) PCT No.: PCT/IB2007/051809
§ 371 (c)(1),
(2), (4) Date: Nov. 25, 2008

(87) PCT Pub. No.: WO2007/141680
PCT Pub. Date: Dec. 13, 2007

(65) Prior Publication Data
US 2009/0171233 A1 Jul. 2, 2009

(30) Foreign Application Priority Data
Jun. 2, 2006 (EP) .................................. 06114879

(51) Int. Cl.
*A61B 5/04* (2006.01)
(52) U.S. Cl. ...................................... 600/546

(58) Field of Classification Search .................. 600/547, 600/587, 595; 442/205–207, 301, 181, 185, 442/186
See application file for complete search history.

(56) References Cited

U.S. PATENT DOCUMENTS

| 7,144,830 B2 * | 12/2006 | Hill et al. ................ 442/205 |
| 2002/0173828 A1 | 11/2002 | Gozani et al. |
| 2003/0069514 A1 | 4/2003 | Brody |
| 2004/0054273 A1 | 3/2004 | Finneran et al. |

FOREIGN PATENT DOCUMENTS

| EP | 1637076 A1 | 3/2006 |
| JP | 2003169782 A | 6/2003 |
| WO | 9014792 A1 | 12/1990 |
| WO | 9846129 A | 10/1998 |
| WO | 2004091389 A1 | 10/2004 |

* cited by examiner

*Primary Examiner* — Brian Szmal
(74) *Attorney, Agent, or Firm* — Larry Liberchuk

(57) ABSTRACT

A biofeedback system and a display device for the use in the biofeedback system. Also disclosed is a method for a biofeedback treatment of a person or an animal. Biofeedback is a therapy method which is used in rehabilitation facilities, for example in the neurological rehabilitation. A neural signal magnitude below a certain threshold does not result in a muscle response, for example, because the provided stimulus is insufficient to trigger the muscle. In order to provide a patient with an intuitive feedback of the sub-threshold neural signal nevertheless, the signal is detected and made recognizable to the patient.

18 Claims, 2 Drawing Sheets

BIOFEEDBACK SYSTEM AND DISPLAY DEVICE

The present invention relates to a biofeedback system and to a display device for the use in the biofeedback system. The present invention further relates to a method for a biofeedback treatment of a person or an animal.

Biofeedback is a therapy method which is used in rehabilitation facilities, for example in neurological rehabilitation. A neural signal magnitude below a certain threshold does not result in a muscle response, for example, because the provided stimulus is insufficient to trigger the muscle. In order to provide a patient with an intuitive feedback of the sub-threshold neural signal nevertheless, the signal is detected and made recognizable to the patient.

In United States Patent Application Publication US 2003/0069514 A1 a monitoring system for bioelectric signals is disclosed. The bioelectric signals, so called electromyography (EMG) signals, are generated during muscle contraction and the energy of the EMG signals is proportional to muscle tone. The system includes a matrix of detection electrode arrays that is positioned on the patient and EMG amplifiers. Regarding biofeedback rehabilitation, one drawback of the known system is that the results of the EMG activity are displayable as data, for example on a PC screen or on a dedicated display of a measuring device. The figures do not mediate to the patient where in his body neural activity is caused by his attempts to move a limb, for example.

It is therefore an object of the present invention to provide an enhanced biofeedback system that enhances the quality of neural signals of a patient more effectively.

The above objective is accomplished by a biofeedback system and a method for a biofeedback treatment, wherein the biofeedback system comprises a display device and a sensor, the sensor comprising a multitude of electrodes, the sensor being provided for being attached to a person or to an animal and the display device being wearable by the person or animal, wherein a neural signal is detectable by the sensor and wherein a spatial distribution of the signal is visually presentable by the display device.

An advantage of the biofeedback system for rehabilitation treatment is, that the neural signals below a certain threshold are detected and visualized to the patient. Although the stimulus is not sufficient to trigger for example a muscle response, the patient's brain recognizes an effect of its stimulus. Repeated exercising with biofeedback advantageously enforces the neural signal and may lead to a signal magnitude above the threshold. The system according to the invention delivers visual information on the neural signal including its spatial distribution, i.e. the patient is enabled to see where neural activity takes place, the visual information advantageously matching the ambition of the patient.

The patient as referred to herein may be a person or an animal as well, though the main focus will lie on human beings.

The sensor comprises a multitude of electrodes, whereas the electrodes are meant to be any detecting elements that are suitable to detect any physical or chemical quantity to be measured in or on the body of a person or an animal, such as voltage, current, temperature, electrical conductivity, mineral content or pheromonal content. According to the invention neural signals are detectable by the sensor. Neural signals as referred to in this application, are meant to be any physical signals that are measurable in or on the body of a human or animal. Preferably the neural signals detectable by the electrodes are bioelectric signals such as electromyography (EMG) signals, electroencephalography signals or electrocardiography signals.

In a preferred embodiment of the invention the electrodes are EMG electrodes. The EMG signals are proportional to muscle tone. Visualizing EMG signals with the inventive biofeedback system advantageously enhances the progress of rehabilitation, for example in the post-stroke rehabilitation.

The inventive system further preferably comprises a processing element, a magnitude and/or a source location of the neural signal being analyzable by the processing element. The detected neural signals from the sensor are fed to the processing element which preferably comprises a microprocessor. Advantageously, the signal which is derived from each electrode is distinguishable, so that not only the signal strength or magnitude, but also a pattern of the detected neural signal over the multitude of electrodes is analyzable.

Though it would be possible that the processing element is an external device, such as a personal computer or laptop computer, which is connected to the system by connecting cables or by wireless connection, such as radio communication, the processing element is preferably arranged in or at the display device. The processing element is advantageously integrated in the system. It is an advantage of the present invention that the system including the processing element, the sensor and the display device is wearable by the patient, i.e. the patient wears the inventive system similarly to an article of clothing. Preferably the inventive system does not comprise any connecting cables to external devices.

Preferably the magnitude of the neural signal between the electrodes is interpolatable by the processing element. The analyzed magnitude and/or a source location pattern of the neural signal is advantageously smoothed. The number of electrodes may advantageously be reduced.

It is possible that the multitude of electrodes of the sensor is individually arrangeable in or at the patients body. However, it is preferred that the multitude of electrodes of the sensor is provided in an arrayed arrangement, i.e. the arrangement of the electrodes relative to each other is preset. The application of arrayed electrodes is less complicated, thus advantageously mistakes are prevented and/or the assignment of highly qualified personnel is reduced.

More preferably the multitude of electrodes of the sensor is arranged on a substrate. The substrate is any kind of carrier means on or in which the multitude of electrodes is mounted, for example a fabric. The sensor according to this preferred embodiment is advantageously also wearable as a piece of clothing.

It is furthermore preferred, depending on the magnitude and/or source location of the neural signal, that the display device is provided to be controllable by the processing element. By using the magnitude and/or source location of the neural signal for controlling the display device, the patient is advantageously provided with a reproduction of the pattern of the detected signal magnitude and/or source location. The intuitive feedback is enhanced when the patient is provided with a detailed image of the effect that his effort to move his impaired limb has on the neural activity inside his body.

Furthermore preferable, the display device is provided as a light emitting textile. A light emitting textile comprises a textile fabric on or in which a number of light sources are mounted and preferably interconnected. For example the light emitting textile comprises a multitude of light emitting diodes (LEDs). A light-emitting diode (LED) is generally a semiconductor device that emits light. As referred to in this application, an LEDs is meant to comprise all applicable embodiments of LEDs. For example, if the emitting layer material of an LED is an organic compound, it is known as an Organic Light Emitting Diode (OLED). The emitting material can be a small organic molecule in a crystalline phase or a polymer. Polymer materials can be flexible, such LEDs are known as Polymer LEDs (PLEDs) or Flexible LEDs (FLEDs). Compared with regular LEDs, OLEDs are lighter, and polymer LEDs can have the added benefit of being flexible.

More preferable, the display device is capable of emitting multiple colors, i.e. the light emitting textile comprises LEDs of different color and/or the LEDs are capable of emitting multiple colors. For example LED units contain two or more diodes of different color. Multiple color LEDs offer the advantage that the magnitude of the neural signal can be displayed by certain colors.

The number of LEDs preferably exceeds the number of electrodes, at least by a factor of two. The display of the interpolated pattern of the magnitude and/or source location of the signal is advantageously enhanced by a higher number of LEDs.

In a preferred embodiment of the invention, the display device is fixedly and detachably arranged relative to the sensor. The display device and the sensor thus form preferably two adjacent layers, which advantageously can be worn as a piece of clothing by the patient. The relative position of the display device and the sensor is fixed, so that the detected and analyzed magnitude and/or source location pattern of the neural signal is reliably displayed in the adequate location.

The display device is preferably attachable to a body part of the person or animal. Advantageously, the display device has the form of a cover or wrap that the patient can wear on or at his impaired limb, for example.

Furthermore preferably, the display device comprises positioning means for repeatedly attaching the display device in a predefined position relative to the body part and/or the sensor. Again, the fixed relative allocation provides a reliable display of the detected signal. For example, the display device may carry position markers, which have to be matched with natural or artificial marks on the body part of the patient.

In a further, preferred embodiment of the invention the system further comprises a data storage, a database being storable in this data storage. The database contains information on the allocation of the electrodes to muscles or muscle groups of the body part for one or more persons or animals. Due to anatomic differences between different patients, the allocation of the electrodes to the muscles may vary from one individual to the other. The accuracy of the displayed pattern of neural activity is advantageously enhanced if this allocation is calibrated. The individual allocation for each patient is stored in the database and is advantageously provided for recall each time the session of this individual patient begins. The data storage is preferably a solid-state electronic flash memory data storage device, also called memory card or flash memory card which is more preferably mounted in or at the display device, together with the processing element.

The present invention further relates to a display device for use with a biofeedback system as described herein before, wherein the display device is provided to be wearable by a person or animal. The advantage of the inventive display device is that neural activity is displayable directly on the body part wherein the neural activity takes place. Another advantage of the wearable display device is, that it may as well be used to signal the gradual fatigue of muscle tissue during electrical stimulation and thus the patient can be prevented from falling.

The display device is preferably provided as a light emitting textile, the light emitting textile comprising a multitude of LEDs. A light emitting textile is easy-weighed and flexible and the patient can advantageously wear the display device like a piece of clothing.

The present invention further relates to a method for a biofeedback treatment of a person or animal, the method comprising the steps of
attaching a sensor with a multitude of electrodes to the person or animal,
attaching a display device to a body part of the person or animal,
detecting a neural signal by the multitude of electrodes and visualizing a spatial distribution of the neural signal on the display device, which is provided as a light emitting textile.

The biofeedback effect in rehabilitation is advantageously enhanced as the patient is enabled to see where his effort to move his impaired limb leads to neural activity.

Preferably, the method further comprises the step of analyzing a magnitude and/or source location of the neural signal and/or, depending on the magnitude and/or source location of the signal, controlling a multitude of LEDs of the display device. A pattern of the magnitude and source location of the detected signals is visualized for the patient, which advantageously refers to the actual neural activity in the body part of the patient.

The display device is preferably attached to the body part and/or the sensor for each treatment of the person or animal in a predefined position. Exact positioning of the display device at the beginning of each session assures reliable display of the neural activity and the results of the sessions are comparable.

The inventive method comprises in a further embodiment the step of determining an allocation of the electrodes and muscles or muscle groups of the body part. By this kind of calibration the detected signals are allocated to certain muscles or muscle groups. This enhances the biofeedback effect, because an adaptation to the most variable anatomy of patients is made possible. The person skilled in the art understands that either the electrodes can be placed such, that they are allocated optimally to the muscles or muscle groups or, for example in the case of an array of electrodes, the processing element is adapted to the given allocation.

Furthermore preferred, the determined allocation of the electrodes and muscles or muscle groups of the body part for each individual person or animal is stored in a database. Still more preferable, the stored allocation of the electrodes and muscles or muscle groups of the body part for the actually treated person or animal is read back from the database at the beginning of each therapy session. Advantageously, the sensor does not have to be calibrated for each session but only once at the beginning of the therapy.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 1:
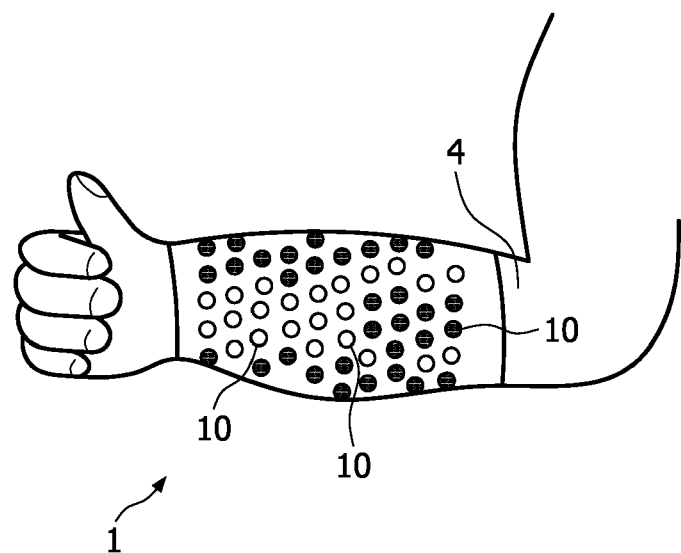
FIG. 1 illustrates schematically an attached display device according to the present invention.

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, a display device 1 is depicted, which is attached to a body part 4, here outlined in the form of an arm of a person. The display device 1 is preferably a light emitting textile 1, also called photonic textile, a fabric that contains lighting devices and can therefore serve as the display device 1. Flexible arrays of multicolored light-emitting diodes LEDs 10 are embedded in the fabric without compromising the softness of the cloth. The light emitting textile 1 can be worn by a person. This is most advantageous, because the light emitting textile 1 can thus be applied to any body part 4 of the patient, whichever is actually treated.

The display device 1 is controlled by a processing element, which is not depicted. The magnitude and/or source location of neural signals in the body part 4 of the patient is displayed on the display device 1. Biofeedback is a rehabilitation method in which sub-threshold neural signals to the muscle are detected, for example by electromyography (EMG) electrodes, and visualized for the patient. Although the stimulus is not sufficient to trigger a muscle response, the patient recognizes the effect of the stimulus through visual perception. Repeated exercising with biofeedback enhances the neural signal quality and may lead to above-threshold neural signals. The use of light emitting textiles worn by the patient on the impaired limb 4, e.g. his arm, allows to visualize the EMG activity in spatial and temporal manner.

Figure 2:
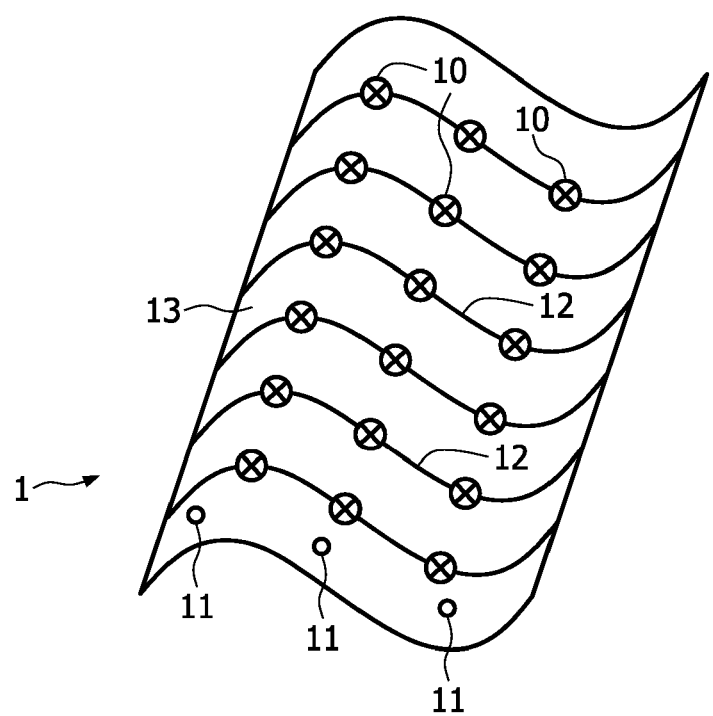
FIG. 2 illustrates schematically a detail of an embodiment of the display device according to the present invention.

In FIG. 2, the display device 1 is depicted, showing details of the light emitting textile 1. Multiple-color LEDs 10 are embedded in a fabric 13, the LEDs interconnected by connection wires 12. For example a red LED signal represents a strong neural signal and a yellow LED signal represents a weak neural signal. Bicolor LED units contain two diodes, one in each direction of current flow and each of a different color, allowing two-color operation by changing polarity, or a range of apparent colors to be created by altering a percentage of time the voltage is in each polarity. Other LED units contain two or more diodes of different colors, arranged in either a common anode or common cathode configuration. These can be driven to different colors without reversing the polarity. Alternatively, the LED units 10 may have an integrated vibrator circuit that makes the LEDs 10 flash. The magnitude of the neural signal could then be displayed by a flashing frequency.

The fabric 13 can be any interconnecting, flexible and/or drapable substrate, made for example entirely or partly of cloth or from plastics and films. In the fabric 13 positioning means 11 are arranged, which are used to attach the display device 1 in the same fixed position on the body part 4 of a patient for every therapy session. The positioning means 11 are for example markers or holes in the fabric 13, which can be matched with natural or artificial marks on the body part of the patient.

Figure 3:
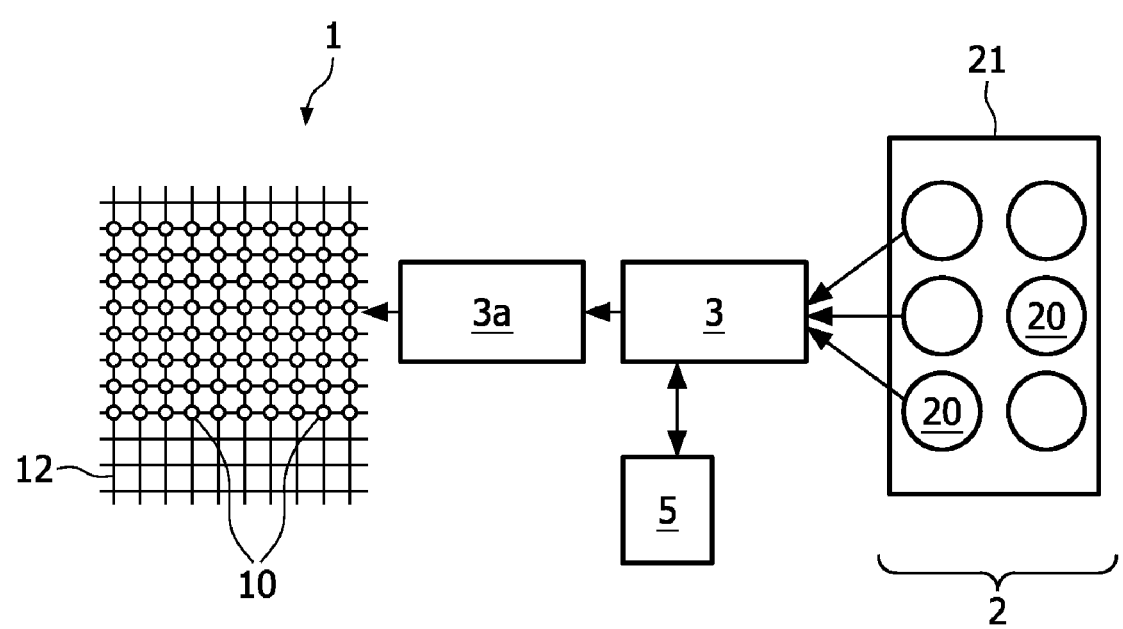
FIG. 3 illustrates schematically an embodiment of a system according to the present invention.

In FIG. 3, a system comprising a sensor 2 and a display device 1 is depicted.

The sensor 2 comprises a multitude of electrodes 20 for example EMG electrodes. The electrodes 20 detect neural signals of the patient, who is not depicted. An arrayed arrangement of the electrodes 20 allows a detection of the magnitude as well as spatial distribution of the neural signal. Each electrode 20 of the sensor 2 is connected to a processing element 3, which analyzes the multitude of measurement signals and generates a pattern of the magnitude and/or source location of the neural signal. The processing element 3 comprises a control unit 3a, which drives the display device 1. The generated pattern of the magnitude and/or source location of the neural signal is input into the control unit 3a and thus the magnitude and/or source location of the neural signal is visualized on the display device 1.

The display device comprises a multitude of LEDs 10, interconnected and connected to the control unit 3a by connecting wires 12. Each electrode 20 is allocated to a number of LEDs 10 as the total number of LEDs 10 in the display device 1 usually exceeds the number of electrodes 20 of the sensor 2. The magnitude between two electrodes 20 is interpolated by the processing element 3 in order to provide a smooth depiction of the detected signal. Further each electrode 20 is allocated to a certain muscle or muscle group of the patient (not depicted). As the anatomy of patients varies, this allocation of the electrodes 20 to the muscles is different for each individual patient. A data storage 5 is connected to the processing element 3, wherein a database is stored. The database comprises data on the allocation of the electrodes 20 to the muscles or muscle groups for each patient. At the beginning of a therapy session the allocation data is read back from the database to the processing element.

The invention claimed is:

1. A biofeedback system, comprising:
a display device, and
a sensor comprising a multitude of electrodes,
wherein the sensor is adapted to form a first layer to be attached to a person or to an animal and the display device is adapted to form a second layer disposed directly on top of the first layer being wearable by the person or animal,
wherein a neural signal is detectable by the sensor and wherein a spatial distribution of the signal is visually presentable by the display device.

2. The system according to claim 1, further comprising a processing element, a magnitude and/or a source location of the neural signal being analyzable by the processing element and/or, depending on the magnitude and/or source location of the neural signal, the display device being controllable by the processing element.

3. The system according to claim 2, wherein the magnitude of the neural signal between the electrodes is interpolatable by the processing element.

4. The system according to claim 2, wherein the processing element is arranged in or at the display device.

5. The system according to claim 1, wherein the multitude of electrodes of the sensor is provided in an arrayed arrangement.

6. The system according to claim 1, wherein the multitude of electrodes of the sensor is arranged on a substrate.

7. The system according to claim 1, wherein the electrodes are EMG electrodes.

8. The system according to claim 1, wherein the display device is provided as a light emitting textile, the light emitting textile comprising a multitude of LEDs.

9. The system according to claim 8, wherein the LEDs are capable of emitting multiple colors.

10. The system according to claim 8, wherein the number of LEDs exceeds the number of electrodes, at least by a factor of two.

11. The system according to claim 1, wherein the display device is fixedly and detachably arranged relative to the sensor.

12. The system according to claim 1, wherein the display device comprises positioning markers or holes for repeatedly attaching the display device in a predefined position relative to the body part and/or the sensor.

13. The system according to claim 1, further comprising a non-transitory data storage, a database being storable in the non-transitory data storage, the database comprising information on the allocation of the electrodes to muscles or muscle groups of the body part for one or more persons or animals.

14. A method for a biofeedback treatment of a person or animal, comprising:
attaching a sensor with a multitude of electrodes to the person or animal,
attaching a display device to a body part of the person or animal,
detecting a neural signal by the multitude of electrodes, and
visualizing a spatial distribution of the neural signal on the display device, which is provided as a light emitting textile;
wherein the display is adapted to form a first layer and the sensor is adapted to form a second layer disposed directly on top of the first layer.

15. The method according to claim 14, further comprising analyzing a magnitude and/or source location of the neural signal and/or, depending on the magnitude and/or source location of the signal, controlling a multitude of LEDs of the display device.

16. The method according to claim 14, further comprising determining an allocation of the electrodes and muscles or muscle groups of the body part.

17. The method according to claim 16, further comprising storing the determined allocation of the electrodes and muscles or muscle groups of the body part for each individual person or animal in a database in a non-transitory data storage.

18. The method according to claim 17, wherein the stored allocation of the electrodes and muscles or muscle groups of the body part for an actually treated person or animal is read back from the database.

* * * * *